United States Patent
Lescano et al.

(10) Patent No.: US 11,463,020 B2
(45) Date of Patent: Oct. 4, 2022

(54) MOVEMENT AMPLIFYING ACTUATION DEVICE

(71) Applicants: CENTRE NATIONAL DE LA RECHERCHE SCIENTIFIQUE (CNRS), Paris (FR); UNIVERSITE DE FRANCHE-COMTE, Besancon (FR); ECOLE NATIONALE SUPERIEURE DE MECANIQUE ET DES MICROTECHNIQUES, Besancon (FR)

(72) Inventors: Sergio Lescano, Besancon (FR); Nicolas Andreff, Ecole-Valentin (FR); Micky Rakotondrabe, Besancon (FR); Kanty Rabenorosoa, Courchapon (FR); Brahim Tamadazte, Besancon (FR); Clément Bouderlique, Belfort (FR)

(73) Assignees: CENTRE NATIONAL DE LA RECHERCHE SCIENTIFIQUE (CNRS), Paris (FR); UNIVERSITE DE FRANCHE-COMTE, Besancon (FR); ECOLE NATIONALE SUPERIEURE DE MECANIQUE ET DES MICROTECHNIQUES, Besancon (FR)

( * ) Notice: Subject to any disclaimer, the term of this patent is extended or adjusted under 35 U.S.C. 154(b) by 355 days.

(21) Appl. No.: 16/634,375

(22) PCT Filed: Jul. 27, 2018

(86) PCT No.: PCT/EP2018/070462
§ 371 (c)(1),
(2) Date: Jan. 27, 2020

(87) PCT Pub. No.: WO2019/020804
PCT Pub. Date: Jan. 31, 2019

(65) Prior Publication Data
US 2021/0114200 A1     Apr. 22, 2021

(30) Foreign Application Priority Data

Jul. 27, 2017    (FR) ..................................... 1757122

(51) Int. Cl.
*H02N 2/00*      (2006.01)
*A61B 34/00*      (2016.01)
(Continued)

(52) U.S. Cl.
CPC ............... *H02N 2/00* (2013.01); *A61B 34/72* (2016.02); *B25J 7/00* (2013.01); *B25J 9/003* (2013.01);
(Continued)

(58) Field of Classification Search
CPC .......... H02N 2/00; H02N 2/046; H02N 2/108; H01L 41/0953; B25J 7/00; B25J 18/005;
(Continued)

(56) References Cited

U.S. PATENT DOCUMENTS 5,219,347 A * 6/1993 Negus .................... A61B 34/72
606/17
6,323,581 B1 * 11/2001 Powell ................. H01H 71/127
310/330
(Continued)

FOREIGN PATENT DOCUMENTS

FR     2362525 A1    3/1978
FR     2850218 A1    7/2004

OTHER PUBLICATIONS

International Search Report issued in Application No. PCT/EP2018/070462, dated Dec. 3, 2018 (6 pages).
(Continued)

*Primary Examiner* — Emily P Pham
(74) *Attorney, Agent, or Firm* — Osha Bergman Watanabe & Burton LLP

(57) ABSTRACT

A movement amplifying actuation device may include two piezoelectric beams, one beam being attached at a fixed
(Continued)

point, and a hinge connecting a first beam and a second beam between them. Each hinge may include a first flexible portion connected to the first beam, a second flexible portion connected to the second beam, a first rigid portion connecting the first and second flexible portions, a second rigid portion capable of being positioned against a fixed point, and a third flexible portion connecting the second beam to the second rigid portion at a pivot point of the second beam such that the assembly formed by the second rigid portion and the second beam forms a lever around the pivot point. The flexible and rigid portions may form a single piece.

20 Claims, 12 Drawing Sheets

(51) Int. Cl.
| | | |
|---|---|---|
| | *B25J 7/00* | (2006.01) |
| | *B25J 9/00* | (2006.01) |
| | *B25J 9/12* | (2006.01) |
| | *H02N 2/04* | (2006.01) |
| | *H02N 2/10* | (2006.01) |

(52) U.S. Cl.
CPC ............... *B25J 9/12* (2013.01); *H02N 2/046* (2013.01); *H02N 2/108* (2013.01)

(58) Field of Classification Search
CPC .. B25J 9/003; B25J 9/12; B25J 9/0015; A61B 34/72
See application file for complete search history.

(56) References Cited

U.S. PATENT DOCUMENTS

| | | | |
|---|---|---|---|
| 6,798,120 B1 * | 9/2004 | Fearing | H02N 2/101 |
| | | | 310/331 |
| 2010/0245966 A1 | 9/2010 | Yasuda | |
| 2014/0265731 A1 | 9/2014 | Storm et al. | |

OTHER PUBLICATIONS

Written Opinion issued in International Application No. PCT/EP2018/070462, dated Dec. 3, 2018 (7 pages).

* cited by examiner

MOVEMENT AMPLIFYING ACTUATION DEVICE

TECHNICAL FIELD OF THE INVENTION

The invention relates to amplified actuation devices, to be more precise miniaturized devices, occupying a volume of the order of ten cubic millimeters.

The invention may find numerous applications, in particular for actuating a platform. That platform may receive a mirror to reflect a laser beam. The laser beam can therefore be used for laser marking and/or etching, for 3D scanning, in the field of (micro)robotics (for example laser vision), in the field of telecommunications (for example for a variable optical attenuator or an optical switch), or for medical applications (relatively non-invasive endoscopic surgery, optical exploration with or without biopsy, etc.).

The invention was specifically developed for laser microsurgery of the vocal cords, or phono-surgery, with the objective of guiding a laser beam precisely toward the vocal cords. The so termed phono-surgery is defined as follows: "all surgical procedures that maintain, restore or improve the human voice", or "the science of manipulating the vibratory elements of the larynx in order to restore the vocal function". This involves the excision of the mass of tissue that could be a benign mass or a cancerous lesion. In laser surgical pharmacy, use of a scalpel is replaced by use of laser technologies.

Although there exists a variety of laser technologies, the widespread conventional method for remote control of the surgical laser is a mechanical manipulator with a surgical microscope positioned in such a manner as to view the vocal cords to be treated, as shown in FIG. 1. This mechanical manipulator and the laser source are located approximately 400 mm from the vocal cords. However, several of the difficulties associated with the use of this conventional mechanical manipulator are linked to the ergonomics of the device. Consequently, the clinician has no practical means for stabilizing their hand whilst effecting the precise and delicate movements necessary to orient the surgical laser in a precise and constant manner. Thus there exists a considerably high risk of burning healthy tissue. Moreover, there exist parts of the vocal cords that are not accessible.

More recently, remote controlled surgical systems have been developed based on a microbot in the form of a system at the end of a flexible and adjustable endoscope (or flexible laryngoscope in the case of the vocal cords) for inserting the microbot and video cameras into the body of the patient, eliminating the need for the surgical microscope and enabling access to the areas not accessible using the previous technique. These laser microsurgical systems offer better accessibility and better precision than the previous systems. There exist for example endoscopic systems employing diffraction of a laser with the aid of prisms or lenses.

However, the existing systems do not offer a sufficient angle to reach all of the vocal cords: the direction of the laser beam that is managed by refraction (using prisms and lenses) has modest angular ranges (approximately 2 degrees).

Moreover, they do not enable a uniform diameter to be delivered, in effect, by refraction, the diameter of the laser spot on the vocal cords changing in accordance with the refraction direction.

Finally, they do not enable precise control of the position of the laser: in effect, to have precise control of the position of the laser it is generally necessary to be able to perceive the position of the laser spot at the level of the vocal cords. However, surgical lasers are all invisible to the naked eye (either ultraviolet or infrared). To remedy this a visible laser is used that is aligned with the direction of the invisible laser. However, a new problem arises: the two laser beams are caused to pass through prisms for guiding them; now, the prisms take into account the wavelength of the light that passes through them to deviate it. Here the two lasers that it is wished to align do not have the same wavelength and are therefore not guided in the same manner by the prism. The exact zone in which the invisible laser operates will therefore not be seen.

The inventors have therefore preferred to opt for a system based on reflection of a laser with the aid of a mirror. The laser beam is reflected by a plane mirror situated on the platform of a microbot. In the ideal configuration the laser beam will be fed by an optical fiber from the outside as far as the distal end of the laryngoscope. In this case a mirror is placed in order to focus the laser beam and at the same time to reflect it on the platform of the microbot. On the platform a plane mirror reflects this laser beam onto the vocal cords. The orientation of the plane mirror is guided by the microbot and remote controlled. Thus the microbot directs the laser onto the vocal cords.

Thus the objective is to develop a complex robot able to respond to the numerous constraints that such surgical intervention raises. In particular, the robot should address the following criteria:
- at least two degrees of freedom to be able to intervene on all the vocal cords;
- distance between the head of the flexible laryngoscope and the vocal cords of 20 mm, implying that a minimum range to be developed by the laser beam is $\pm 25°$ for each axis (a circle of approximately 20 mm diameter), which corresponds to an angular range of $\pm 12.5°$ for each rotation axis of the mirror;
- resolution of the laser scanning of the vocal chord better than 100 µm, so as not to risk damaging healthy cells when treating malignant cells: this is equivalent to approximately $0.15°$ of resolution in each angle of rotation of the mirror at the reference distance of 20 mm;
- a bandwidth of at least approximately 200 Hz: the speed of movement of the beam and therefore of the mirror must be sufficient not to risk damaging the healthy tissue of the vocal cords; in fact, the laser being a system for ablation of the cells to be treated and having a high power, it must not remain for long at the same location in order not to damage adjoining cells that could be healthy cells; a maximum time of passage must therefore be respected that is expressed in the form of a minimum bandwidth;
- biocompatibility: as the flexible laryngoscope and the head that encloses the microbot are intended to work in spaces in vivo, the equipment must use materials that are either biocompatible or protected by biocompatible materials to ensure that they are not in contact with human tissue;
- focusing system: to enable good detection of the laser spot by the video cameras and to enable high resolution on the vocal cords, its specified diameter is 200 µm;
- size of the microbot: it must fit within a cube of less than $10 \times 10 \times 10$ mm$^3$.

This complex robot must provide at least the following two functions: the function of orienting the mirror according to two rotation axes and in the required angular range, and the function of remote actuation of said rotation to achieve the required angular range, with a precision (resolution) and a minimum speed of movement (bandwidth) complying with the criteria referred to above.

The invention concerns the second function, that is to say the function of remote actuation of said rotation.

Thus the objective is to provide an actuation device that enables actuation of an object in accordance with a given minimum amplitude, precisely and at speed, that actuation device having to fit within a cube of less than 10×10×10 mm³.

PRIOR ART

Actuation devices (also known as actuators) convert an electrical, thermal, magnetic or other type of energy into movements or mechanical loads. Actuators are key components in robotics. In micro-mechanisms, the word usually employed to designate an actuator is "micro-actuator". Micro-actuators are often constituted of active or intelligent materials that must typically provide a micrometric or sub-micrometric resolution. Active materials have required characteristics such as high resolution and/or high bandwidth. Moreover, most of them can also be used as detectors or sensors.

The dimensions of a micro-actuator are generally less than 10 mm.

The micro-actuators most suited to the criteria mentioned above are piezoelectric micro-actuators. There is employed the phenomenon of piezoelectricity that causes electrical charges to appear on the surfaces of a material when it is exposed to a mechanical load—this is what is termed the direct piezoelectric effect—and conversely a deformation is obtained if an electric field is applied. It is this converse effect that is exploited for an actuator.

Piezoelectric micro-actuators offer high resolution (up to a few nanometers), a high bandwidth (up to tens or hundreds of kilohertz) and a high force density compared to other intelligent materials, which renders them suitable for the design of micro-actuators.

As shown in FIGS. 2a, 2b and 2c, these are structures 90 of rectangular section, preferably in a cantilever configuration.

These structures comprise different layers, also known as blades, stuck to one another; when there are two blades the term two-layer structure is used.

These structures comprise an active layer 91, comprising a piezoelectric material, the active layer 91 being sandwiched between two electrodes 94, 95 adapted to excite the active piezoelectric material. In this case the term unimorph structure is used (FIG. 2b).

A unimorph structure may comprise an additional layer, termed the passive layer, which may be a layer of a supple or flexible material, and may be fixed against one of the electrodes. In a unimorph structure a passive layer makes it possible to generate the curvature of the beam that can be exploited when energizing the active layer. This passive layer may be conductive and function as an electrode.

These structures may comprise a plurality of active layers, for example. The term bimorph structure is used if there are at least two active layers 91, 92 (FIG. 2a). Each active layer 91, 92 is sandwiched between two electrodes 94, 95, 96 adapted to excite the active piezoelectric material. The bimorph beams enable greater movements. The term multimorph structure is more generally used if there are two or more active layers.

A multimorph structure may also comprise an additional layer, termed the passive layer. The passive layer in a multimorph structure helps to increase the stiffness of the structure.

Means 150 must be provided for electrical energization of the electrodes to excite the piezoelectric materials.

A structure 90 of the above kind may be termed: piezoelectric beam, or beam comprising a piezoelectric element.

To be configured as a cantilever, as shown in FIG. 2c, one end 90a of the beam 90 is fixed and the other end 90a flexes on either side of a reference position termed the rest position. A piezoelectric beam is therefore able to flex about said rest position, up to a maximum angle $\alpha_{max}$ corresponding to an amplitude of flexing of approximately 150 to 200 µm for a beam 10 mm×2 mm×0.3 mm made of a PZT-5A piezoelectric material in a bimorph structure.

The amplitude of the movement in flexing (or the angle $\alpha_{max}$) is a function of:
- the dimensions of the beam (length and thickness; the width rather enabling sizing of the applicable force);
- the morphology of the beam (unimorph, bimorph, etc.);
- the voltage applied between the electrodes.

The greater the required amplitude of the movement in flexing (or the angle $\alpha_{max}$), the lower the speed (or the frequency) of movement, and vice versa. In other words, known micro-actuators do not address the two-fold constraint of amplitude and speed (or frequency).

Now, amplitudes are required of the order of a millimeter, whilst minimizing the dimensions of the beam and the applied voltage, and whilst maintaining a good movement dynamic of the beam.

Movement amplifiers have therefore been looked for.

The patent document FR2850218 describes an amplified movement piezoelectric actuator comprising a mechanical movement amplifier connected to a load and to a base and having an elliptical shell shape made from a deformable elastic material and piezoelectric elements mounted inside said shell in the direction of the major axis of the shell and excited electrically to produce longitudinal deformation of said major axis and to induce deformation of the minor axis intended to generate at the interface with the load a movement the component of which along the minor axis is amplified.

The aforementioned patent document employs stack type piezoelectric actuators, that is to say another form of piezoelectric actuation. Stack piezoelectric actuators do not use the two-layer structure effect, but a movement obtained directly by deformation of the piezoelectric material. The dimensions of the stacks are relatively large and the movements generated are very small, although they offer a much higher force than two-layer structure beams. Their object is to improve the capacity to damp a piezoelectric actuator and its resistance to external dynamic forces.

Moreover the amplified movement piezoelectric actuator according to the above patent document is a system constrained in terms of amplitude and speed of movement by its shell structure.

There thus exists a real need for an actuator device, in particular a micro-actuator, offering both a high speed of movement (for example a speed corresponding to a response time of 1 ms) and a high amplitude of flexing (for example of the order of a millimeter), that is to say much greater than known micro-actuators allow.

Moreover, the amplitudes delivered must also be precise and it must be possible to control them with a precision for example of the order of 50 µm per 1 mm.

SUMMARY OF THE INVENTION

To solve the aforementioned problem, the invention consists in a movement amplifying actuation device, characterized in that it comprises:
- a first beam comprising a piezoelectric element, adapted to flex about a principal axis when a voltage is applied to it and adapted to be attached at a first end to a first fixed point;
- a second beam comprising a piezoelectric element, adapted to flex about said principal axis when a voltage is applied to it, and having a first end and a second end;
- a first articulation comprising:
  - a first portion flexible about a first axis perpendicular to the principal axis and connected to the first beam at the second end of said first beam,
  - a second portion flexible about a second axis perpendicular to the principal axis and connected to the second beam at the first end of said second beam,
  - a first rigid portion connecting the first and second flexible portions,
  - a second rigid portion adapted to be positioned against a second fixed point,
  - a third portion flexible about a third axis perpendicular to the principal axis connecting the second beam to the second rigid portion at a pivot point of said second beam so that the assembly formed by the second rigid portion and the second beam forms a lever about said pivot point, said flexible portions and rigid portions being parts of a one-piece component.

By "articulation" must be understood a means of assembling two beams that enables articulation with one or two degrees of freedom. That articulation enables the movements of the beams to be amplified.

The device is configured so that the cumulative effects of the flexing received by the segment between the pivot point and the first end of the second beam and the flexing of said second beam when a voltage is applied to it generates a flexing movement amplified in the segment between the pivot point and the first end of said second beam.

The first end of said second beam is a free end, which may be connected to a system to be actuated.

In some embodiments the movement amplifying actuation device further comprises:
- a third beam comprising a piezoelectric element, adapted to flex about the principal axis when a voltage is applied to it and having a first end and a second end;
- a second articulation comprising:
  - a first portion flexible about an axis perpendicular to the principal axis and connected to the second beam at the second end of said second beam,
  - a second portion flexible about an axis perpendicular to the principal axis and connected to the third beam at the first end of said third beam,
  - a first rigid portion connecting the first and second flexible portions,
  - a second rigid portion adapted to be positioned against a third fixed point,
  - a third portion flexible about a third axis perpendicular to the principal axis connecting the third beam to the second rigid portion at a pivot point of said third beam so that the assembly formed by the second rigid portion and the second beam forms a lever about said pivot point,
- said flexible portions and rigid portions being parts of a one-piece component.

In the above configuration three beams are interconnected by two articulations with one or two degrees of freedom.

In the above configuration the third beam has a free first end that may be connected to a system to be actuated.

This configuration is of particular interest in that it enables amplification of the flexing imparted to the third beam, the second beam forming an intermediate amplifier.

In some embodiments the movement amplifying actuation device comprises:
- a first beam comprising a piezoelectric element, adapted to flex about a principal axis when a voltage is applied to it and adapted to be attached at a first end to a first fixed point;
- N other beams, N being greater than or equal to 2 and M varying between 2 and N, each $M^{th}$ beam comprising a piezoelectric element and being adapted to flex about the principal axis when a voltage is applied to it, and having a first end and a second end; the $N^{th}$ beam having a free second end;
- X articulations, X being equal to N−1 and Y being equal to M−1, each $Y^{th}$ articulation comprising:
  - a first portion flexible about an axis perpendicular to the principal axis and connected to the $Y^{th}$ beam at the second end of said $Y^{th}$ beam,
  - a second portion flexible about an axis perpendicular to the principal axis and connected to the $M^{th}$ at the first end of said $M^{th}$ beam,
  - a first rigid portion connecting the first and second flexible portions,
  - a second rigid portion adapted to be positioned against an $M^{th}$ fixed point,
  - a third portion flexible about an axis perpendicular to the principal axis connecting the $M^{th}$ beam to the second rigid portion at a pivot point of said $M^{th}$ beam so that the assembly formed by the second rigid portion and the $M^{th}$ beam forms a lever about said pivot point.

In the above configuration, a plurality of beams are interconnected by a triple articulation with one or two degrees of freedom.

In the above configuration the first beam is connected at a first end to a fixed point and the $N^{th}$ beam has a free first end.

Said free end of the $N^{th}$ beam may be connected to a system to be actuated.

The above configuration is of even more particular interest in that it enables amplification of the flexing imparted to the last beam.

Moreover, producing common wiring may be envisaged, even if the system loses one degree of freedom in actuation.

Not actuating certain beams that retain a mechanical amplification capacity may also be envisaged. By actuating or not actuating certain beams of the active structure, it could be possible to manage and/or to refine the precision, the response time and/or the amplitude of flexing.

In some embodiments, a $Y^{th}$ articulation further comprises a third rigid portion and a fourth rigid portion forming with the other parts of said articulation a one-piece component:
- the third rigid portion forming the connection between the first flexible portion of said $Y^{th}$ articulation and the $Y^{th}$ beam,
- the fourth rigid portion forming the connection between the second flexible portion of said $Y^{th}$ articulation and the $M^{th}$ beam.

In some embodiments, the flexible portions of at least one $Y^{th}$ articulation have parallel articulation axes perpendicular to the principal axis.

In some embodiments, the piezoelectric element comprises lead zirconate titanate. Lead zirconate titanate (PZT) is a piezoelectric material that is advantageous because its biocompatibility has been proven under certain conditions.

In some embodiments, one beam has a bimorph structure. In this case it comprises two piezoelectric elements. This enables greater flexing of a beam.

The invention also concerns a spherical parallel kinematic microbot with two degrees of freedom, comprising:
- a spherical orientation device with two degrees of freedom comprising a platform to be oriented about a first rotation axis and a second rotation axis relative to a fixed base, a first actuation arm and a second actuation arm;
- first and second movement amplifying actuation devices according to the invention;
  - the first actuation device being connected to the first actuation arm so as to transmit to it a first movement in translation relative to the fixed base so as to drive the platform in rotation about the first rotation axis, and
  - the second actuation device being connected to the second actuation arm so as to transmit to it a second movement in translation relative to the fixed base so as to drive the platform in rotation about the second rotation axis.

In some embodiments, the orientation device is a spherical orientation device with two degrees of freedom connecting a platform to two fixing points of a fixed base so as to be able to orient said platform in space by rotation about a first axis and a second axis, these two axes being substantially perpendicular and crossing at a center of spherical movement situated in said member to be oriented, comprising:
- a first actuation arm configured to effect a movement in translation relative to the fixed base and adapted to apply to a first transmission arm connected to a first fixing point of the fixed space by a flexible connection articulated about the first axis a movement in rotation relative to said fixed base so as to transmit to the platform a movement in rotation about said first axis;
- an intermediate arm connected to the first transmission arm by a flexible connection articulated about a third axis perpendicular to the first and second axes and connected to the platform by a flexible connection so as to transmit to the platform a movement in rotation about the first axis;
- a second actuation arm configured to effect a movement in translation relative to the fixed base and adapted to apply to a second transmission arm connected to a second fixing point of the fixed base by a flexible connection articulated about the second axis a movement in rotation relative to said fixed base so as to apply to the platform a movement in rotation about said second axis, said arm being connected to the platform by a flexible connection articulated about the first axis so as not to drive said second transmission arm in rotation about the first axis during actuation of the first actuation arm;
- the connection between the platform and intermediate arm being articulated about the axis so as not to drive said intermediate arm in rotation about the second axis during actuation of the second actuation arm;
- and the arms, the flexible connections and the platform forming the parts of a one-piece component forming the device, the arms and the platform being rigid portions of the device, and the flexible connections being flexible portions each forming a hinge about one only of the first, second and third axes, and connecting said rigid portions to one another, to the fixed base.

In some embodiments, the rigid portions comprise a central layer of a flexible material, such as a polyimide, sandwiched between two layers of a rigid material, such as carbon fiber, the flexible connections being composed of the central layer.

In some embodiments, one or more transmission arms and/or intermediate arms form a circular arc.

In some embodiments, the spherical orientation device further comprises a flexible connection articulated about an axis parallel to the first axis and disposed between the first actuation arm and the first transmission arm and forming with the arms, the flexible connections and the platform a one-piece component.

In some embodiments, the first actuation arm comprising a first portion adapted to be coupled to the actuation device according to the invention and a second portion connected to the first transmission arm by a flexible connection articulated about an axis parallel to the first axis, said first and second portions being connected by a flexible connection articulated about an axis parallel to the first axis and forming with the arms, the flexible connections and the platform a one-piece component.

In some embodiments, the spherical orientation device further comprising a flexible connection connecting the second actuation arm and the second transmission arm articulated about an axis parallel to the second axis and forming with the arms, the flexible connections and the platform a one-piece component.

In some embodiments, the spherical orientation device further comprises a universal joint type double flexible connection connecting the second actuation arm and the second transmission arm articulated about an axis parallel to the first axis and an axis parallel to the second axis and forming with the arms, the flexible connections and the platform a one-piece component.

In some embodiments, the second actuation arm comprises a first portion adapted to be coupled to the actuation device according to the invention and a second portion connected to the second transmission arm by a single flexible connection or a double flexible connection, the first and second portions and being connected to a universal joint type double flexible connection articulated about an axis parallel to the first axis and an axis parallel to the second axis, and forming with the arms, the flexible connections and the platform a one-piece component.

In some embodiments, the platform of the spherical orientation device supports a mirror.

In some embodiments, the mirror is disposed so as to reflect a laser beam.

In some embodiments, the microbot further comprises a device for viewing a spot of the laser beam positioned on a surface.

DESCRIPTION OF THE FIGURES

The invention will be better understood and other advantages will become apparent on reading the following description, which is given by way of nonlimiting illustration, and in the light of the following appended figures.

The drawings are provided by way of example and are not limiting on the invention. They constitute theoretical diagrammatic representations intended to facilitate an understanding of the invention and are not necessarily to the scale of practical applications.

DETAILED DESCRIPTION OF PARTICULAR EMBODIMENTS

Figure 1:
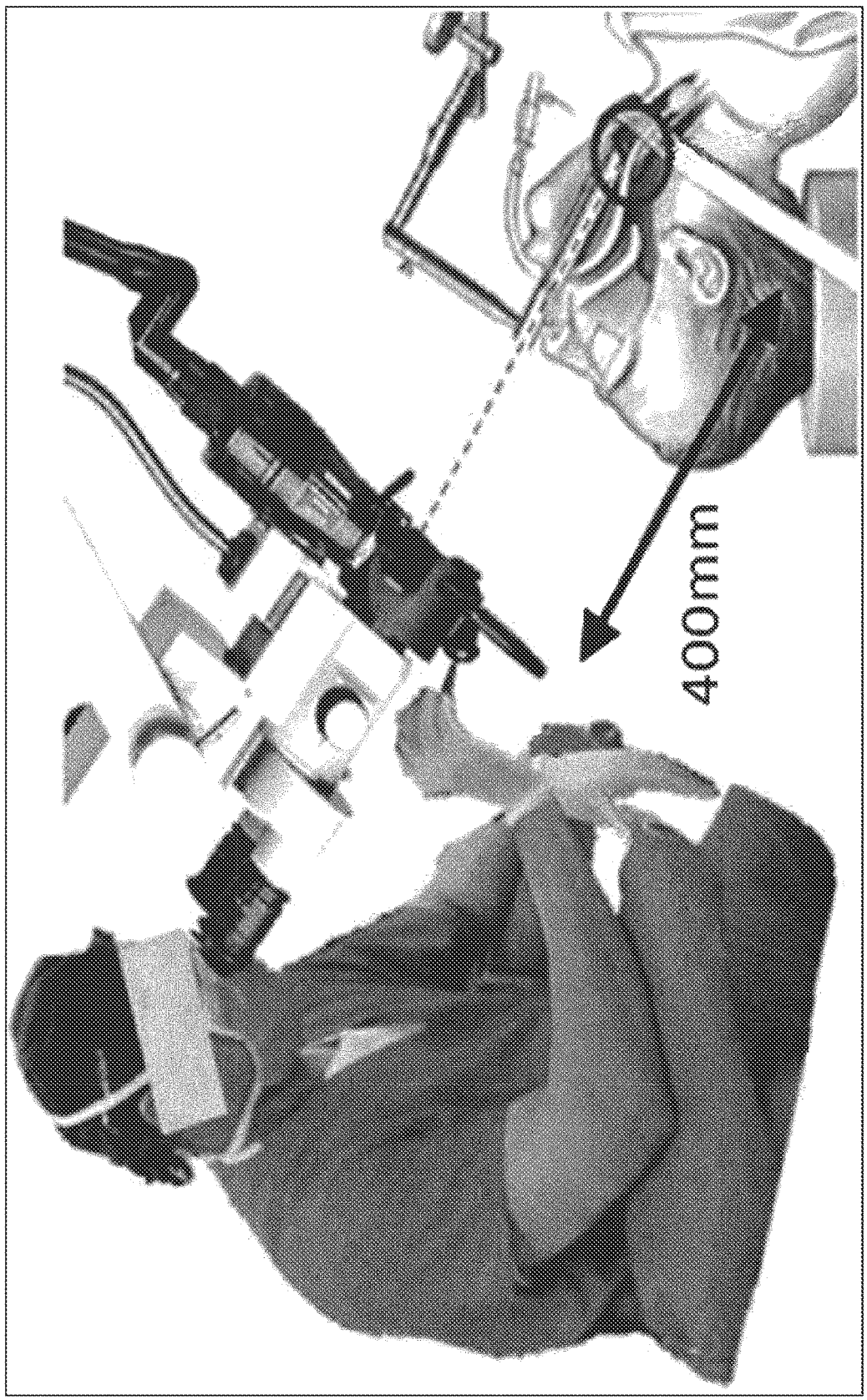
FIG. 1 shows a prior art laser microsurgery method.

FIG. 1 shows a prior art laser microsurgery method that was described in the introduction to the present application and will not be described again here.

Figure 2A:
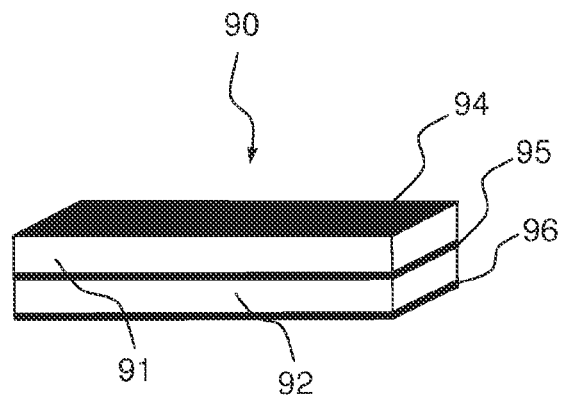
FIGS. 2a, 2b and 2c show prior art bimorph or unimorph piezoelectric structures.
Figure 2B:
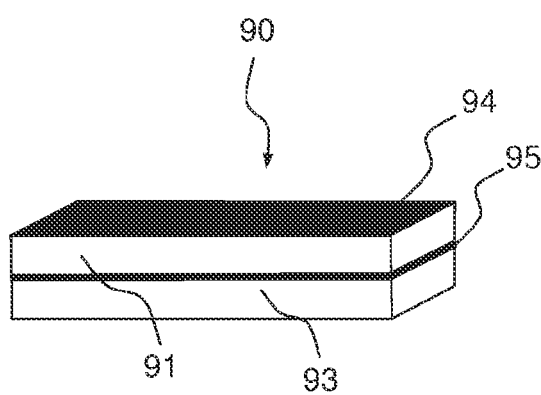
Figure 2C:
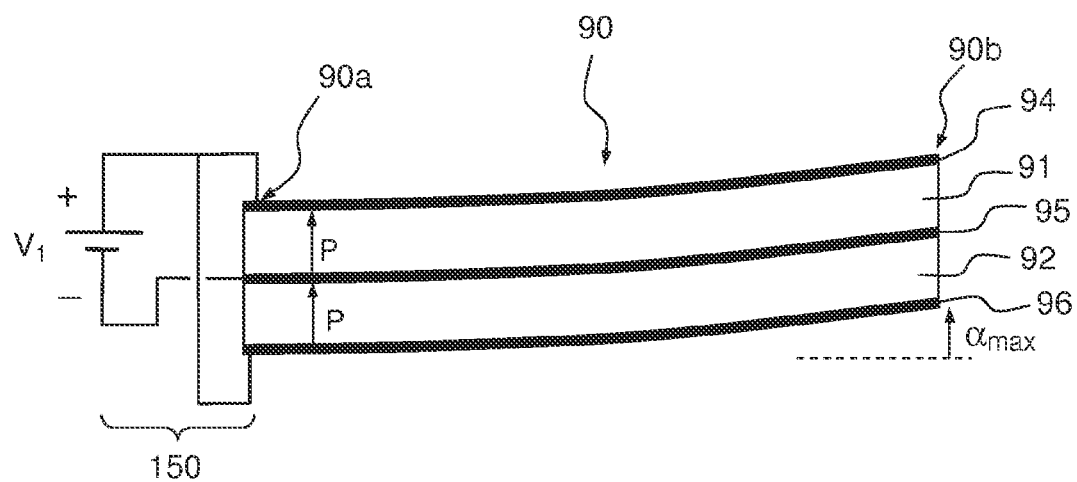

FIGS. 2a, 2b and 2c, which show examples of prior art bimorph or unimorph piezoelectric beams, were described in the introduction to the present application and will not be described again here.

Figure 3A:
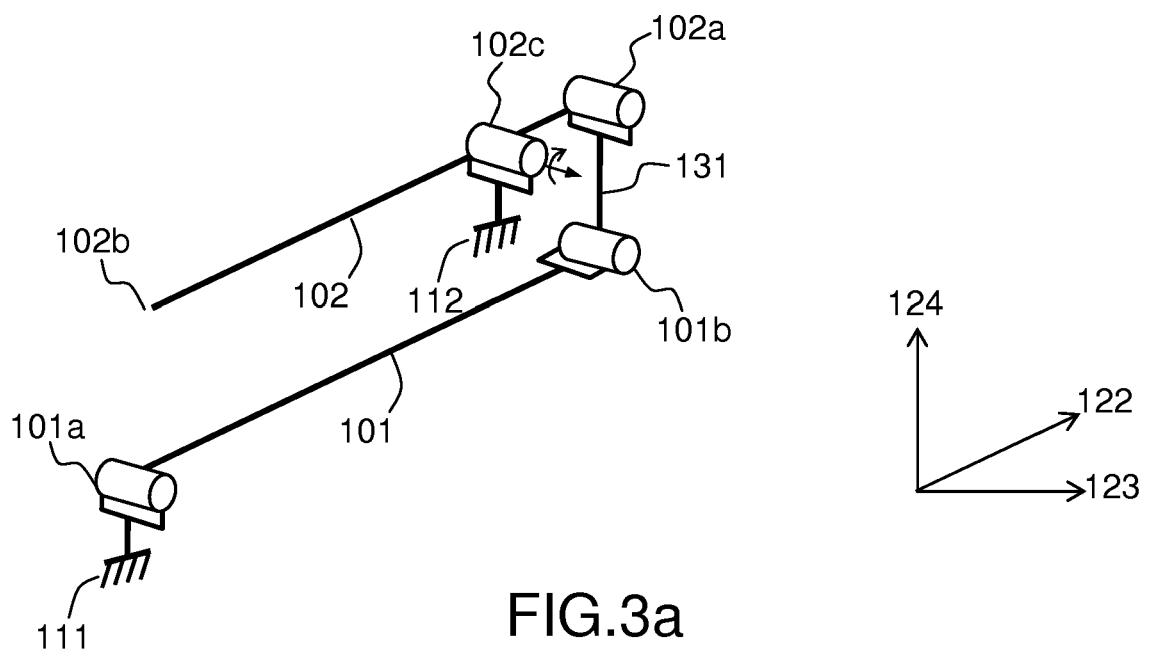
FIGS. 3a and 3b show diagrammatically in 3D two examples of an actuation device according to the invention, the first with two beams and the second with three beams.
Figure 3B:
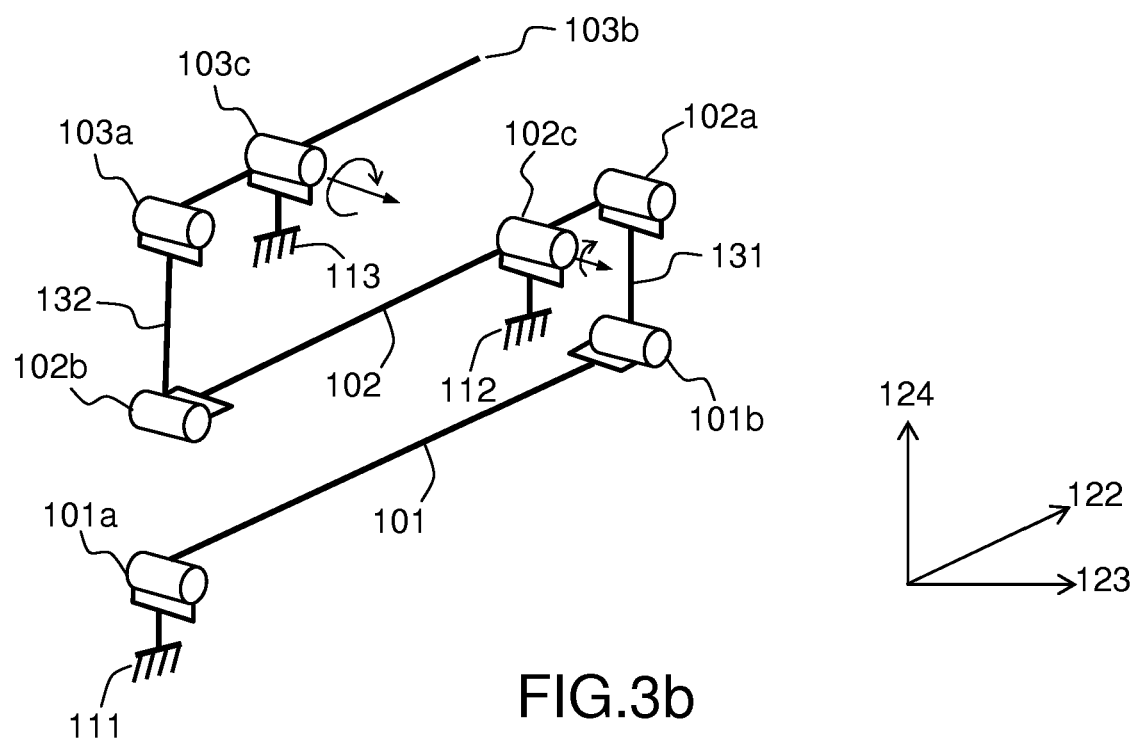

FIGS. 3a and 3b provide 3D theoretical diagrams of two actuation devices according to the invention, the first with two beams and the second with three beams. They will be described at the same time as FIGS. 4a and 4b which are diagrammatic 2D views of the same two examples and further indicate the movements in flexing. These figures are kinematic views.

Figure 4A:
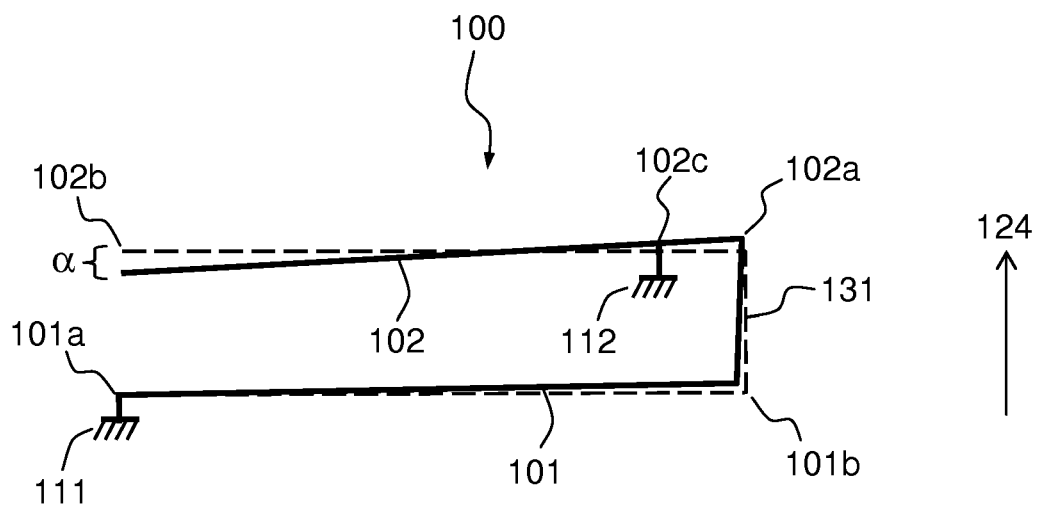
FIGS. 4a and 4b show diagrammatically in 2D the same two examples of actuation devices with their flexing movements amplified, the first with two beams and the second with three beams.

The actuation device represented in FIGS. 3a and 4a comprises a first piezoelectric beam 101 adapted to flex about a principal axis 124 when a voltage is applied to it attached at a first end 101a to a fixed point 111 and a second piezoelectric beam 102 also adapted to flex about the principal axis 124 when a voltage is applied to it. A second end 102b of the second beam 102 is a free end and a first end 102a of the second beam 102 is connected to the first beam 101 by a first articulation 131.

Thus the actuation device 100 comprises a first articulation 131 with one or two degrees of freedom connects the first and second beams 101 and 102. It also enables positioning of the second beam 102 against a fixed point 112, which enables a lever effect to be obtained at the level of a point 102c of the second beam 102.

In the example shown, the first articulation 131 has only one degree of freedom. In other words, it allows rotation between the beams 101 and 102 about only one axis, in this example the axis 122 perpendicular to the principal axis 124.

Figure 4B:
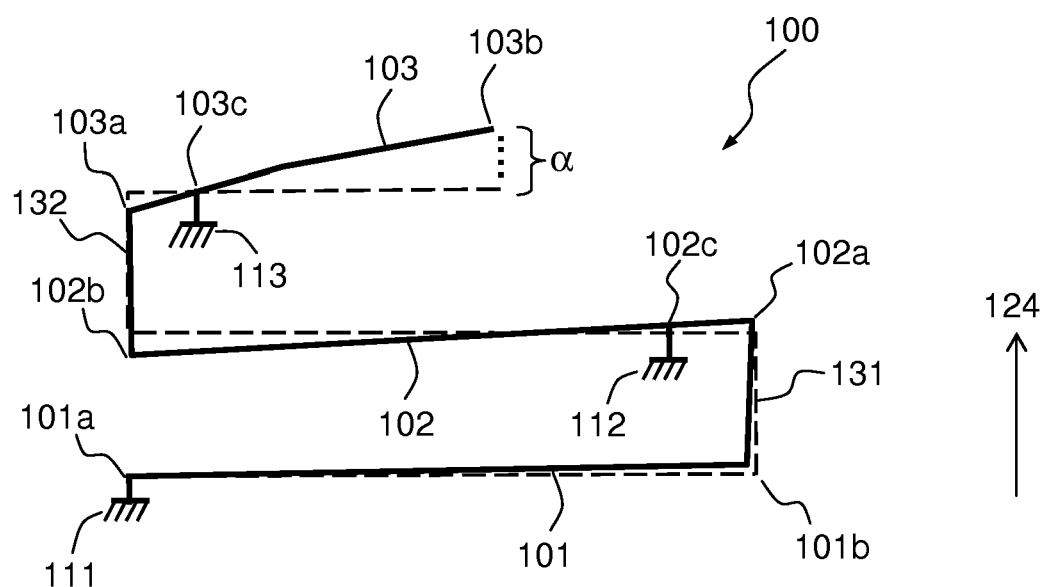

The actuation device represented in FIGS. 3b and 4b further comprises a third piezoelectric beam 103 adapted to flex about the principal axis 124 when a voltage is applied to it. A second end 103b of the third beam 103 is a free end. In this case, the second end 102b of the second beam 102 is not a free end but connected to the third beam 103 by way of a second articulation 132.

Thus the actuation device 100 comprises a second articulation 132 with one or two degrees of freedom connects the second and third beams 102 and 103. It also enables positioning of the third beam 103 against a fixed point 113, which enables a lever effect to be obtained at the level of a point 103c of the third beam 103.

In the example shown the second articulation 132 has only one degree of freedom. In other words, it allows rotation between the beams 102 and 103 about only one axis, in this example the axis 122 perpendicular to the principal axis 124.

This configuration is of particular interest in that it enables amplification of the flexing imparted to the third beam 103, the second beam 102 forming an intermediate amplifier.

The articulations 131 and 132 are produced by means of particular connections, termed flexible connections, described hereinafter.

The actuation device 100 according to the invention is constituted of a set of articulations 131 (respectively 132) with one or two degrees of freedom connecting two piezoelectric beams 101 and 102 (respectively 102 and 103), each of these articulations being a one-piece component, and being formed of single flexible connections and rigid portions, each rigid portion being positioned between two flexible portions.

It is therefore important to understand how a single flexible connection is configured and produced that constitutes the basis for the production of the actuation device 100 according to the invention.

Figure 5:
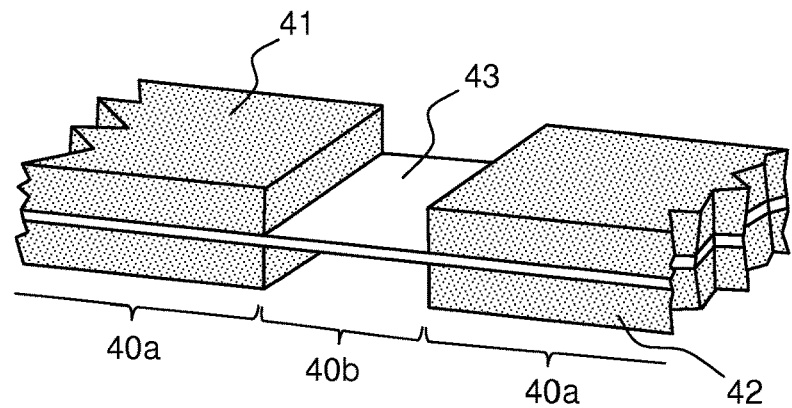
FIG. 5 shows the detail of a flexible portion between two rigid portions of an actuation device according to the invention.

FIG. 5 shows the detail of a flexible connection which represents a detail of an actuation device according to the invention.

A flexible connection 40, which might also be termed a bendable joint, is defined as a flexion hinge formed by a thinner part 40b of a component so as to furnish relative rotation between two rigid portions 40a of the same component adjacent to said thinner part 40b.

In the example shown the component comprises a flexible layer 43 of polyimide and first and second carbon fiber rigid layers 41, 42. The flexible portion 40b corresponds to the width of the flexible layer 43 of polyimide that is not sandwiched between the first and second rigid layers 41, 42. That corresponds to an opening that has been produced in the rigid layers 41 and 42, as explained hereinafter.

Figure 6A:
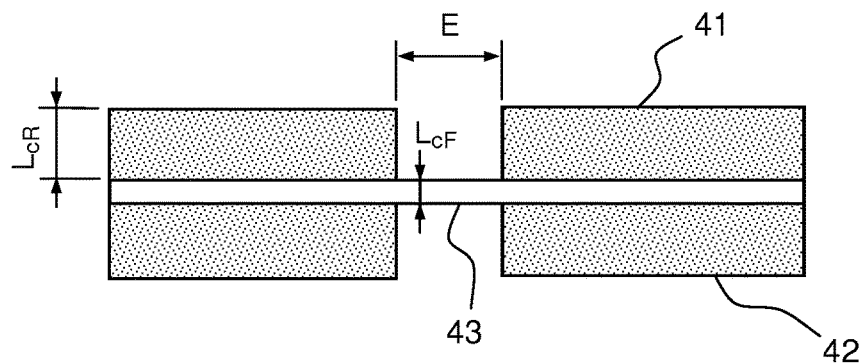
FIGS. 6a and 6b show the dimensions of a flexible portion between two rigid portions as shown in FIG. 5.
Figure 6B:
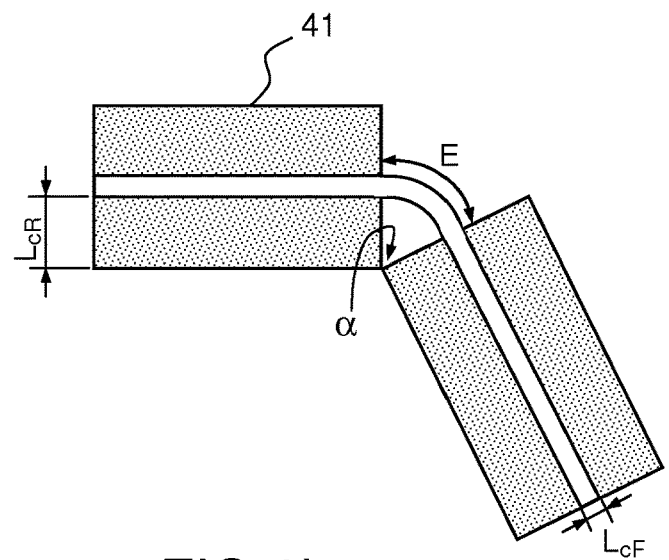

FIGS. 6a and 6b show the dimensions of a flexible connection 40. A flexible connection, also known as a bendable joint, may be sized by modifying the gap E that corresponds to the width of the flexible layer 43 that is not sandwiched between the two rigid layers 41 and 42 and on the sum of the thickness $L_{CR}$ of one rigid layer 41 and the thickness $L_{CF}$ of the flexible layer 43. The angle $\alpha_{max}$ that the bendable joint 43 is able to develop depends on E and on $L_{CR}$ according to the following formula:

$$E = \alpha_{max} \times (L_{CR} + L_{CF})/2 \times f \text{ where:}$$

$L_{CR}$ is the thickness of a rigid material layer,
$L_{CF}$ is the thickness of the flexible layer, and
f is the risk factor taken into account to prevent the hinge jamming in the event of a manufacturing defect. It is generally set at 1.1.

The thickness $L_{CF}$ of the flexible layer is generally not taken into account because it is often negligible compared to the thickness $L_{CR}$ of the rigid layer.

Thus these flexible connections can easily be sized to obtain the angle $\alpha_{max}$ to be developed.

Figure 7A:
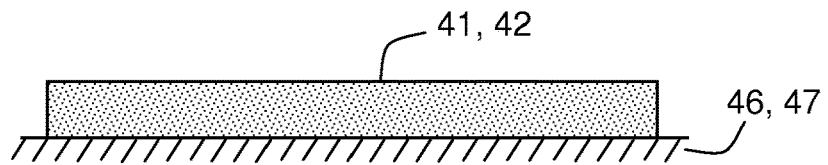
FIGS. 7a, 7b, 7c, 7d and 7e show an example of a method of producing the detail shown in FIG. 5.
Figure 7B:
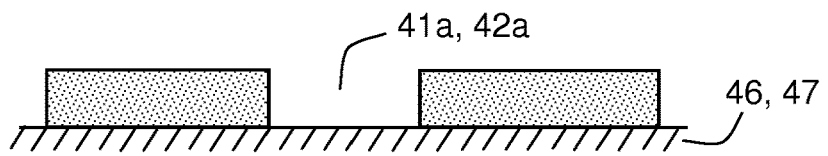
Figure 7C:
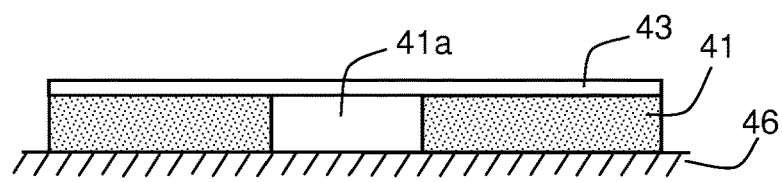
Figure 7D:
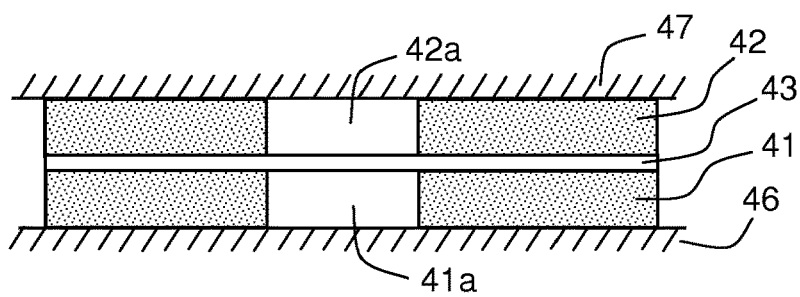
Figure 7E:
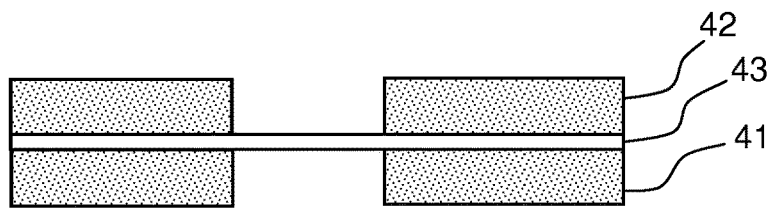

FIGS. 7a to 7e show an example of the method of producing a flexible connection 40 as shown in FIG. 5. The production method comprises the following steps:

a) positioning a first rigid layer 41, for example a carbon fiber layer 130 µm thick, on a first support 46 and a second rigid layer 42, for example a carbon fiber layer 130 µm thick, on a second support 47 (FIG. 7a);

b) micromachining each rigid layer 41, 42 in order to create a void 41a, 42a throughout the thickness of the carbon rigid layer $L_{CR}$ and over a given width E that is the same for both rigid layers 41, 42 (FIG. 7b);

c) fixing, for example sticking, a flexible layer 43, for example a polyimide layer 10 µm thick, onto the first rigid layer 41 including the void (FIG. 7c);

d) adjusting the second rigid layer 42 with the void on the flexible layer 43 fixed to the first rigid layer 41 so that the voids 41a and 42a of the two rigid layers 41 and 42 are face to face, and thereafter fixing, for example sticking, the second rigid layer 42 onto the flexible layer 43 (FIG. 7d);

e) micromachining the resulting composite structure 40 so as to free it from the supports 46 and 47 (FIG. 7e).

The resulting composite structure or flexible connection 40 can thus be articulated about a rotation axis as shown in FIG. 6. Said technique for producing the flexible connections 40 with one degree of freedom enables large flexing angles to be produced.

Each carbon fiber rigid layer 41, 42 can be produced by hardening a carbon fiber film with the aid of a heatset resin heated in a furnace.

Between steps d) and e), the composite structure obtained may be placed in a furnace and heated so as to be solidified, and during this step pressure may be applied to the structure to maintain the new structure united and to prevent undulations.

Laser micromachining is advantageously used by virtue of its capacity to machine with precision a great variety of materials: most metals, ceramics, plastics, carbon fibers. There may be used for example a femtosecond laser (a few hundred femtoseconds) or a DPSS (diode-pumped solid-state) laser.

One of the two laser micromachining methods described hereinafter may be used:

by focusing the laser beam: the laser ray is focused onto a point on the material of the component. The laser point is then moved on the axes x, y or z to enable portions thereof to be vaporized. This method is preferred because it is more direct and faster.

by projection onto a mask: a mask pattern is placed between the laser source and the part to be machined. This method enables vaporization of only the non-hidden parts. It is generally used for surface designs. To obtain a considerable depth the operation is repeated several times.

Figure 8A:
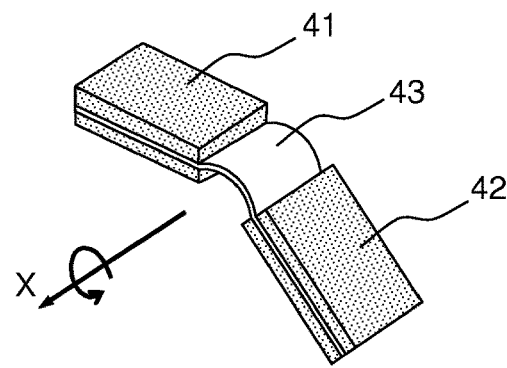
FIGS. 8a, 8b and 8c show articulations according to the invention.
Figure 8B:
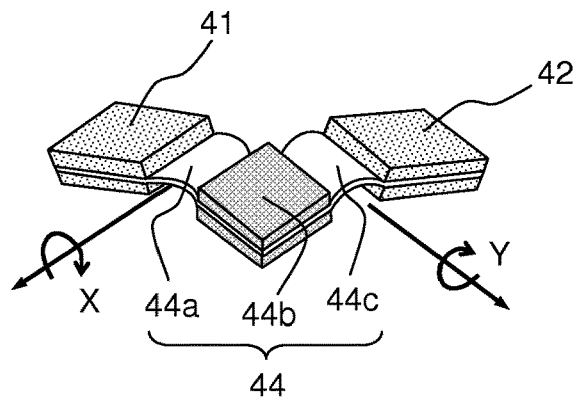
Figure 8C:
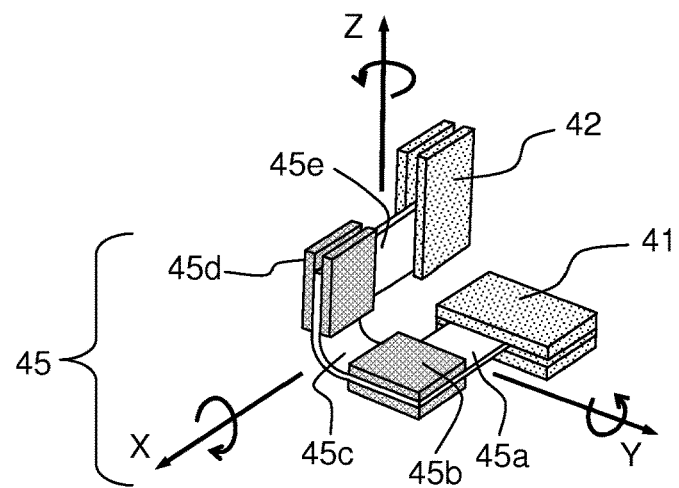

FIGS. 8a, 8b and 8c show articulations according to the invention. The articulations according to the invention are termed flexible connections or bendable joints.

The production of the actuation device according to the invention 100 according to the invention is based on the use of flexible connections that replace the conventional articulations, as shown in FIGS. 8a to 8c.

These single flexible connections may be combined and arranged to produce more complex articulations.

As shown in FIG. 8a, a pivot connection (revolute joint) having one degree of freedom (rotation about the axis x) is provided by a single articulation or single flexible connection 40 described above with reference to FIGS. 5, 6a and 6b. This type of connection is interchangeably termed a "single flexible connection" or "flexible connection" in the present patent application.

As shown in FIG. 8b, a ball-joint connection of finger or universal joint type with two degrees of freedom (rotation about the axes x and y) is provided by a system combining a first flexible connection 44a providing an articulation about the axis x between the first rigid portion 41 and an intermediate rigid portion 44b and a second flexible connection 44c about the axis y between the intermediate rigid portion 44b and the second rigid portion 42. In other words, these are two single flexible connections each oriented about one of the two rotation axes x and y. This connection may be termed a "double flexible connection" or "double flexible connection with two degrees of freedom".

As shown in FIG. 8c, a ball-joint or spherical joint connection with three degrees of freedom (rotation about the axes x, y and z) is provided by a system combining a first flexible connection 45a providing an articulation about the axis y between the first rigid portion 41 and a first intermediate rigid portion 45b, a second flexible connection 45c about the axis x between the first intermediate rigid portion 45b and a second intermediate rigid portion 45d, and a third flexible connection 45e about the axis z between the second intermediate rigid portion 45d and the second rigid portion 42. In other words, these are three single flexible connections each oriented about one of the three rotation axes x, y and z. This connection may be termed a "triple spherical flexible connection" or a "triple flexible connection with three degrees of freedom".

These three types of connections advantageously replace conventional connections for devices with millimeter dimensions.

The micro-actuation device 100 according to the invention employs three flexible connections configured to produce a pivot (or universal joint) type articulation with one (or two) degree(s) of freedom.

Figure 9A:
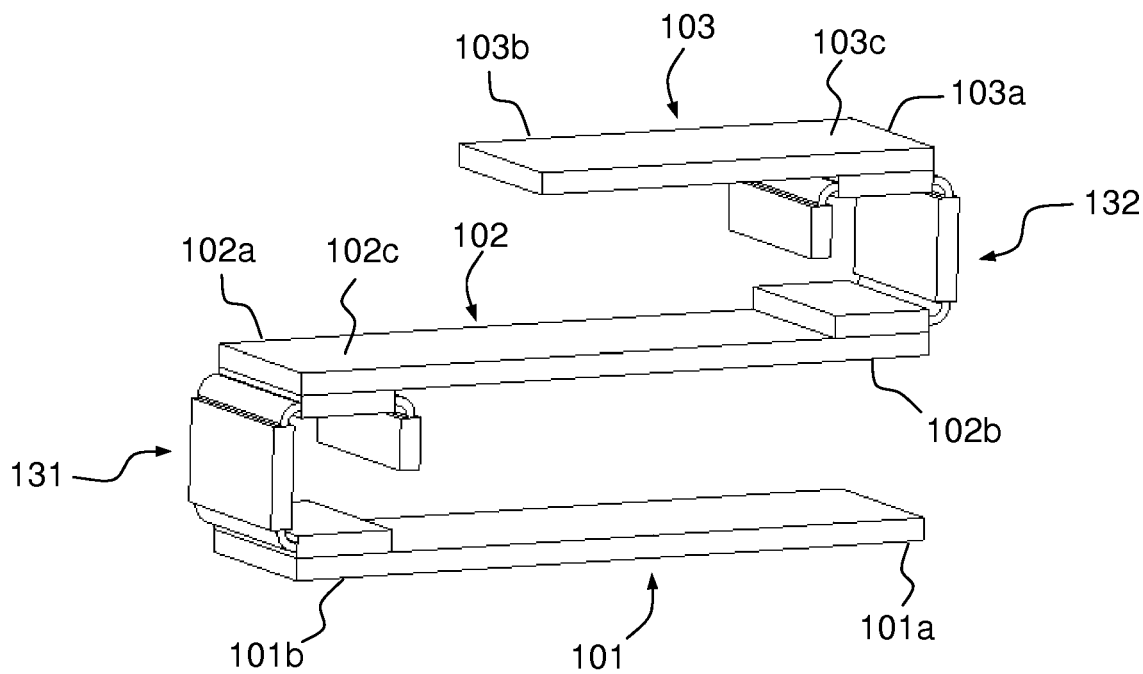
FIGS. 9a, 9b show an example of an actuation device according to the invention in 3D from two different angles.
Figure 9B:
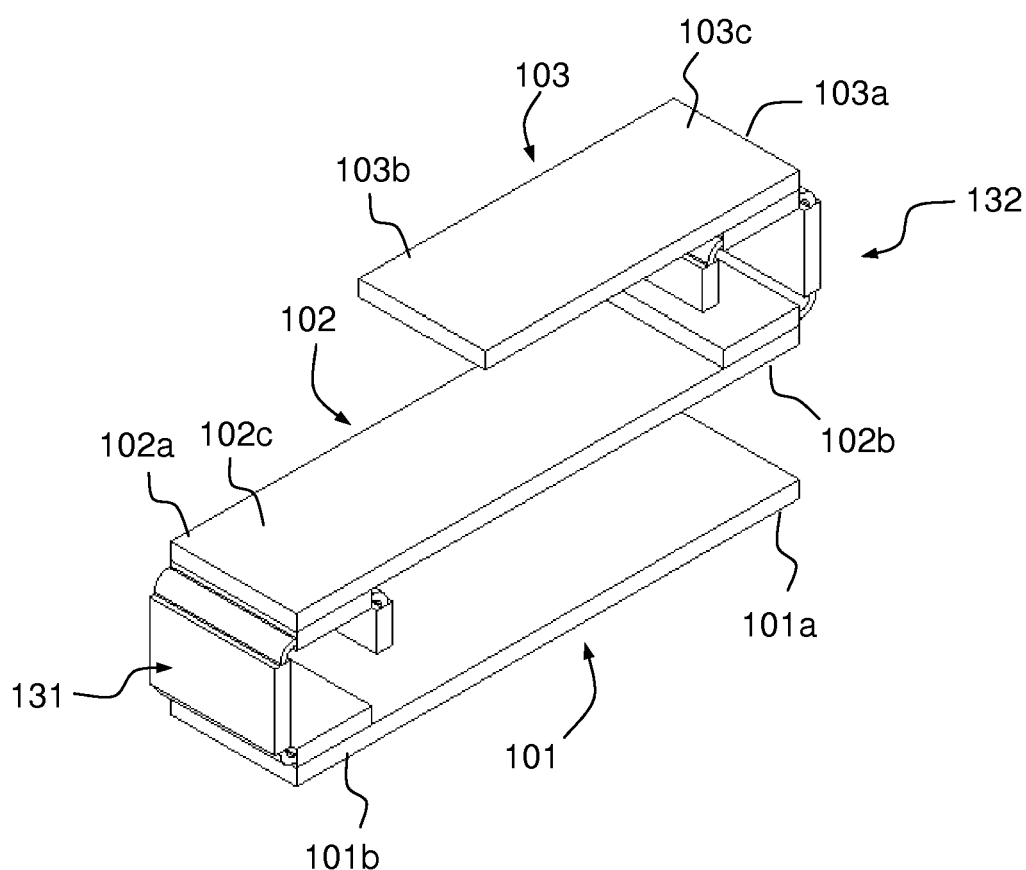
Figure 10:
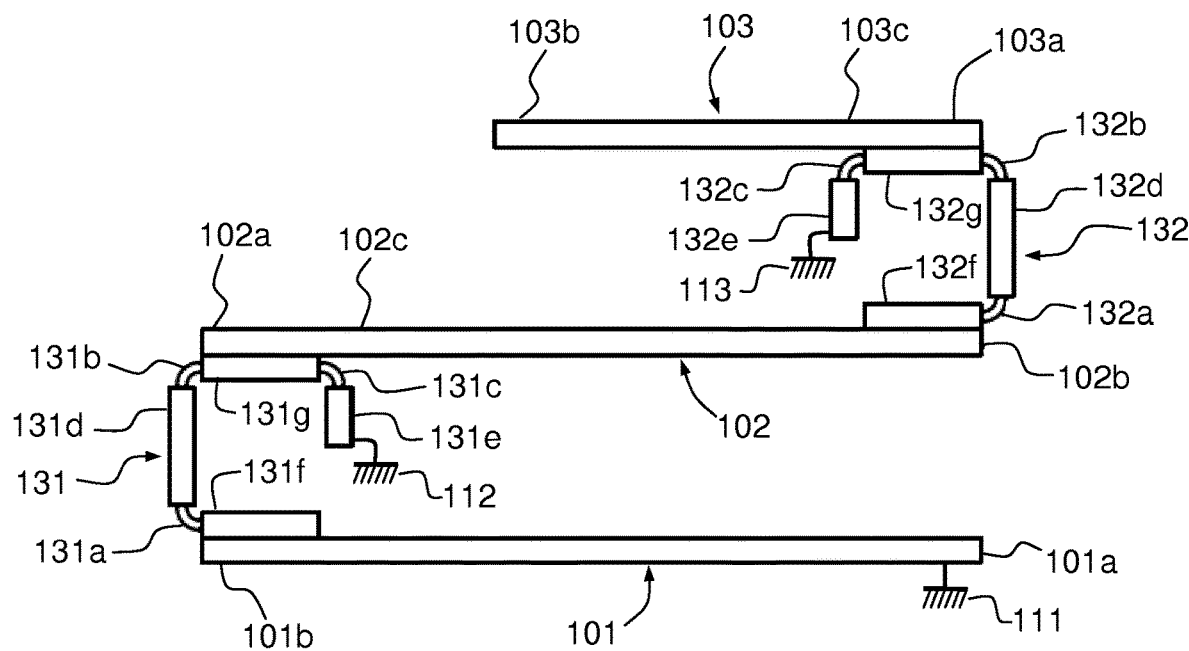
FIG. 10 shows in 2D an example of an actuation device according to the invention.

FIGS. 9a and 9b show in 3D an example of an actuation device 100 comprising three beams seen from two different angles. FIG. 10 is a 2D view of the same example. They represent the example of an actuation device 100 shown kinematically in FIGS. 3b and 4b, with more detail of the flexible connections that were described with reference to FIGS. 5, 6a, 6b, 7a to 7c and 8a to 8e.

The first articulation 131 comprises a plurality of parts 131a, 131b, 131c, 131d, 131e, 131f and 131g that are the parts of a one-piece component:

a first flexible portion 131a connected to the first beam 101 via a third rigid portion 131f, a second flexible portion 131b connected to the second beam 102 via a fourth rigid portion 131g, a first rigid portion 131d connecting the first and second flexible portions 131a and 131b, a second rigid portion 131e that can be positioned against a second fixed point 112, a third flexible portion 131c connecting the second beam 102 to the second rigid portion 131e at the level of the pivot point 102c: the assembly formed by the second rigid portion 131e and the second beam 102 therefore forms a lever about a pivot point 102c of the second beam 102.

The flexible portions 131a, 131b and 131c are single flexible connections 40 all of which are articulated about axes parallel to one another and perpendicular to the principal axis 124.

The second articulation 132 comprises a plurality of parts 132a, 132b, 132c, 132d, 132e, 132f, 132g which are the parts of a one-piece component:

a first flexible portion 132a connected to the second beam 102 via a third rigid portion 132f, a second flexible portion 132b connected to the third beam 103 via a fourth rigid portion 132g, a first rigid portion 132d connecting the first and second flexible portions 132a and 132b, a second rigid portion 132e that can be positioned against a third fixed point 113, a third flexible portion 132c connecting the fourth rigid portion 132g to the second rigid portion 132e at the level of the pivot point 103c: the assembly formed by the second rigid portion 132e and the third beam 103 therefore forms a lever about a pivot point 103c of the third beam 103.

The flexible portions 132a, 132b and 132c are single flexible connections 40 all of which are articulated about axes parallel to one another and perpendicular to the principal axis 124.

In order to finalize the production of the actuation device 100 according to the invention, the flexible connections that constitute a constituent part of the articulations in the actuation device are assembled to the piezoelectric beams.

Thus in the example shown:

the first triple connection 131 is connected to the first beam 101 by fixing, for example sticking or welding, its third rigid portion 131f at the level of the second end 101b of the first beam and is connected to the second beam 102 by fixing, for example sticking or welding, its fourth rigid portion 131g at the level of the first end 102a of the second beam, the second triple connection 132 is connected to the second beam 102 by fixing, for example sticking or welding, its third rigid portion 132f at the level of the second end 102b of the second beam 102 and is connected to the third beam 103 by fixing, for example gluing or welding, its fourth rigid portion 132g at the level of the first end 103a of the third beam 103.

Each beam is then electrically connected.

Figure 11A:
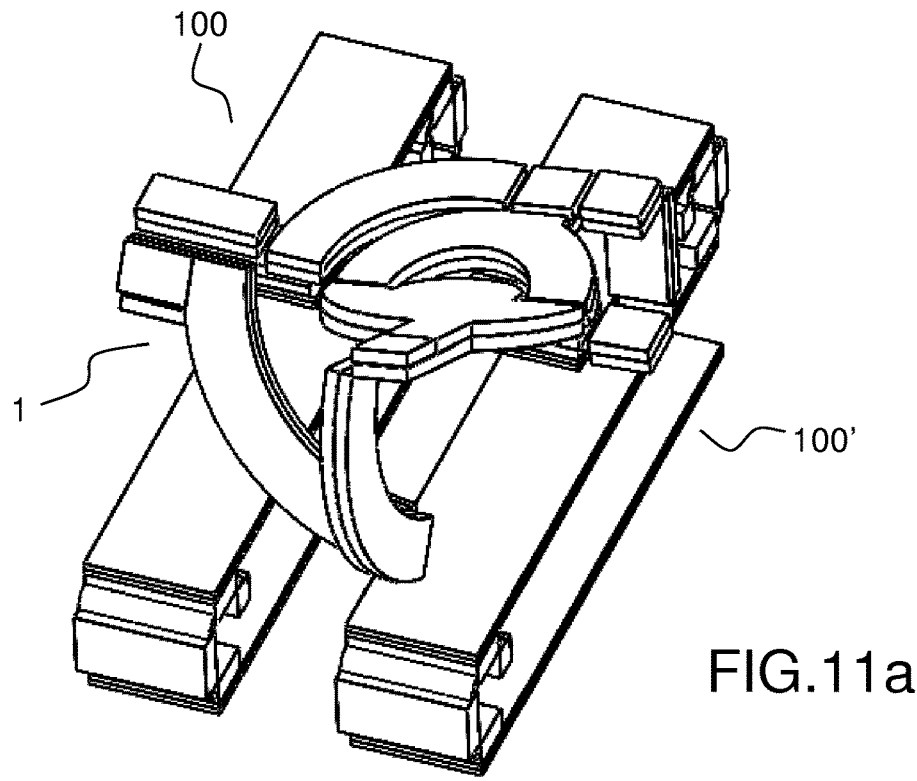
FIGS. 11a, 11b are two different 3D views of an example of a microbot according to the invention without the support.
Figure 11B:
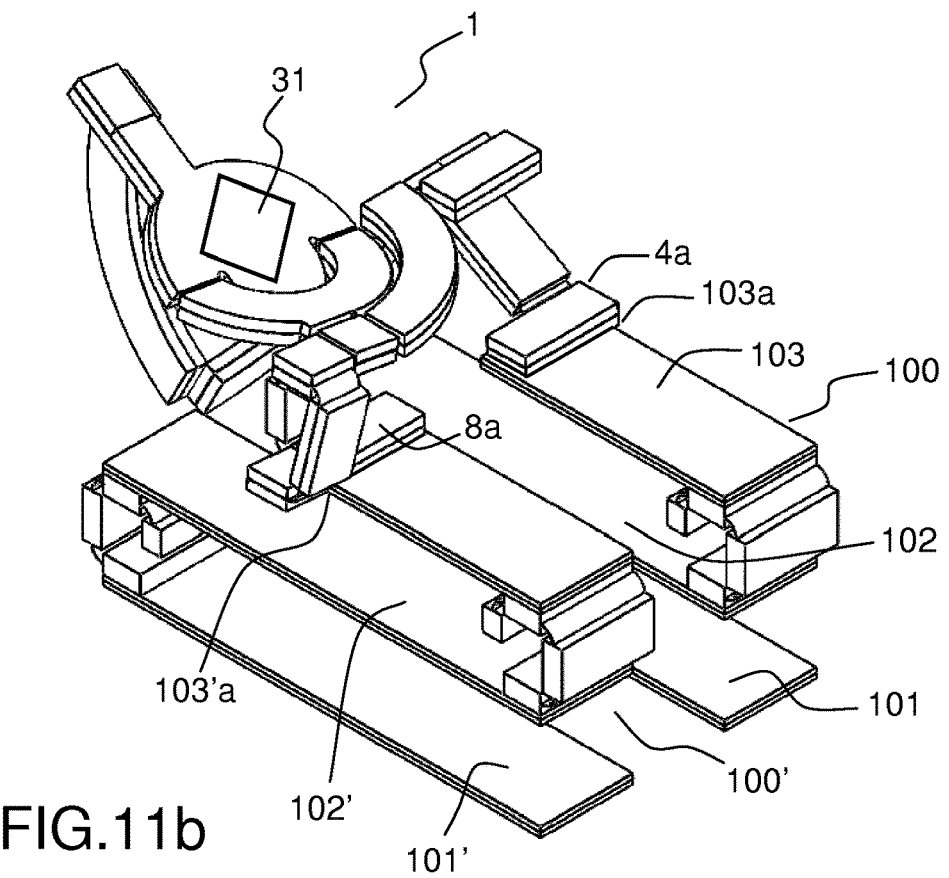

FIGS. 11a, 11b show in two different 3D views an example of a microbot according to another aspect of the invention before fitting the support.

Figure 11C:
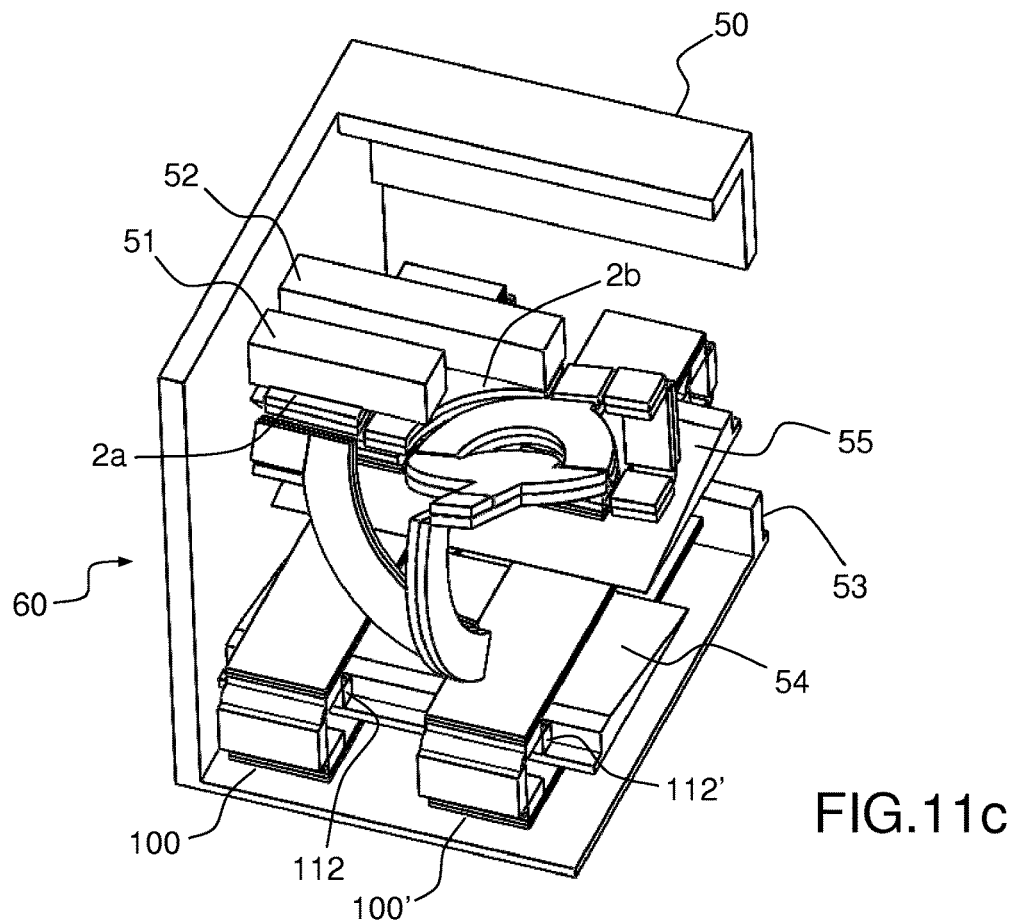
FIGS. 11c, 11d show two different 3D views of an example of a microbot according to the invention with the support.
Figure 11D:
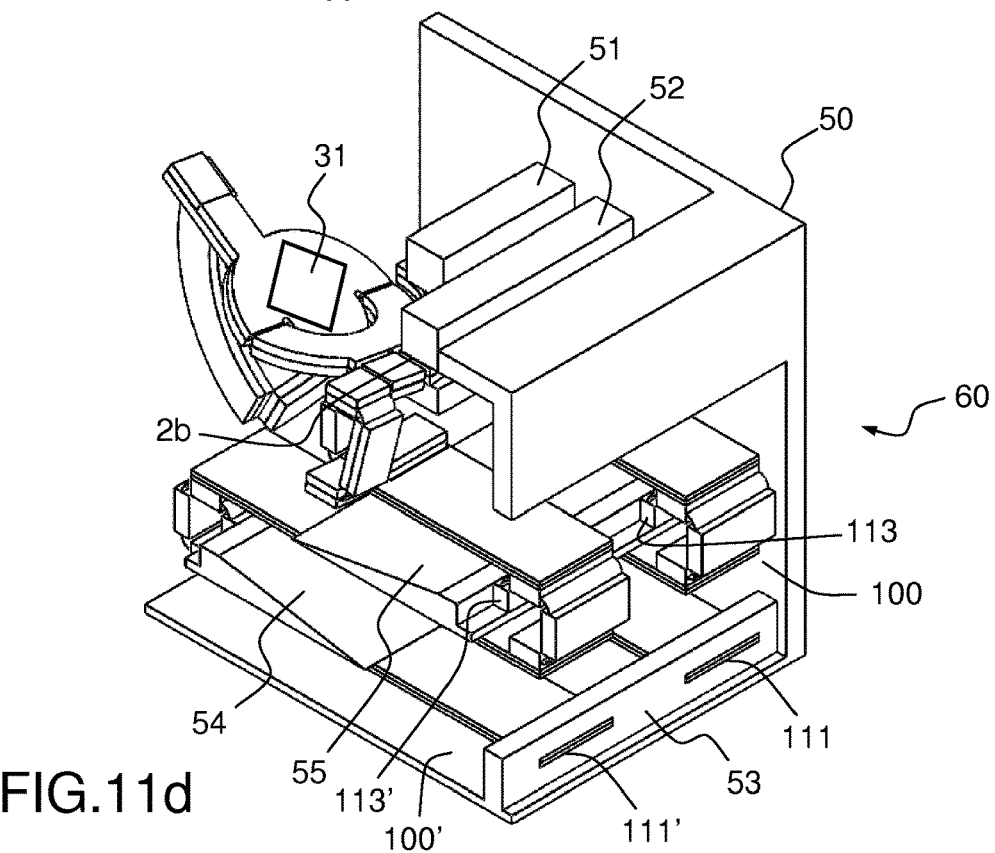

FIGS. 11c, 11d show in two different 3D views an example of a microbot according to the invention, with its support.

A spherical orientation device 1 comprising a platform 30 to be oriented about two rotation axes 22, 23 is combined with at least two actuation devices 100, 100' according to the invention, a first actuation device 100 enabling actuation of the orientation device 1 so as to orient the platform 30 about a first rotation axis 22 and a second actuation device 100 enabling actuation of the orientation device 1 so as to orient the platform 30 about a second rotation axis 23.

A combination of this kind connecting a spherical orientation device 1 and two actuation devices 100, 100' according to the invention enables production of a spherical parallel kinematic microbot with two degrees of freedom parallel to two degrees of freedom addressing the expected constraints and referred to in the introduction to the present application, in particular the precision of orientation, whilst maintaining the required orientation angle ranges.

The actuation devices 100, 100' according to the invention further enable remote actuation of a spherical orientation device 1 since they are connected electrically, and therefore potentially remotely, and act in flexion when they are excited by a voltage.

In the example shown in FIGS. 11a, 11b, 11c, 11d, the spherical orientation device 1 comprises:

a first actuation arm 4 a first portion 4a of which is coupled to a first actuation device 100 according to the invention, to be more precise to the free part 103b corresponding to the second end of the third beam 103 of said actuation device 100; and a second actuation arm 8 a first portion 8a of which is coupled to a second actuation device 100' according to the invention, to be more precise to the free part 103'b corresponding to the second end of the third beam 103' of said actuation device 100'.

This enables the structure shown in FIGS. 11a and 11b to be obtained.

The fixed point 111 (respectively 111') and the fixed pivot points 112, 113 (respectively 112', 113') necessary for the operation of the actuation device 100 (respectively 100') according to the invention form part of the support 50. Said support 50 is also configured to create the fixed points 2a and 2b for the spherical orientation device 1, as shown in FIGS. 11c and 11d.

To be more precise the support 50 comprises a plurality of parts 51, 52, 53, 54, 55 configured to create the fixed parts for the microbot 60. For example:

the part 53 enables creation of the fixed points 111 and 111' for the first beams 101 and 101' of the actuation devices 100 and 100', the part 54 enables creation of the fixed pivot points 112 and 112' for the second beams 102 and 102' of the actuation devices 100 and 100', and the part 55 enables creation of the fixed pivot points 113 and 113' for the third beams 103 and 103' of the actuation devices 100 and 100', the parts 51 and 52 being configured to create the fixed points 2a and 2b for the spherical orientation system 1.

The resulting microbot 60 has a parallel architecture structure which, unlike a serial architecture structure, can employ flexible joints disposed inside said structure that are not necessarily actuated, that is to say passive joints. To the contrary, the flexible joints of the structures in series must all be provided with an actuation device.

Moreover, this makes it possible to save space. This combination therefore enables a microbot to be obtained the dimensions of which fit in a cube of 10×10×10 mm$^3$ maximum, with details on the pattern of tens of µm.

A mirror 31 may be positioned on the platform 30 of the spherical orientation device 1, as shown in FIGS. 11a to 11d. Thus the microbot 60 enables orientation of the mirror 31 about the two rotation axes 22 and 23.

Electrical connections (not shown in the figures) necessary for remote control of the actuation devices 100, 100' and in the end for the rotation of the mirror 31 are added. The electrical connections may be fixed to the support 50, or even wholly or partly inside the support, in order to minimize the volume occupied by the microbot 60 and its electrical connections.

Alternatively, kinematic structures other than spherical structures may be used. In general any kinematic structure able at least to orient a platform about two coplanar axes. Parallel and serial structures are possible.

Figure 12:
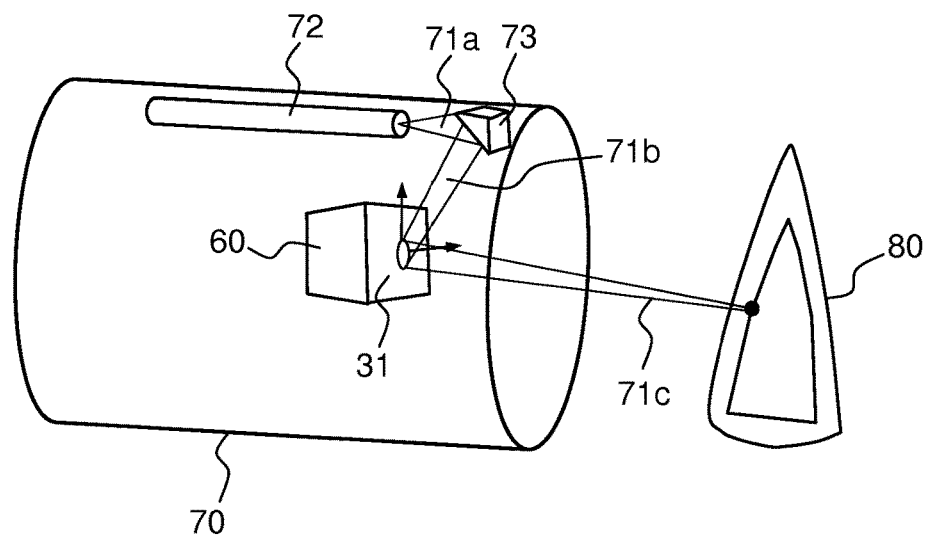
FIG. 12 shows a first example of application of the microbot according to the invention.

As shown in FIG. 12, the microbot according to the invention may be used in the microsurgery field as a system at the end of a flexible endoscope 70. In the specific field of phono-surgery, the endoscope is termed a laryngoscope.

In this case, the microbot carrying the mirror 31, generally a microbot comprising a platform that supports a mirror, is used to orient a laser beam 71. The initial orientation of the mirror 31 must be calculated at the stage of the geometrical design of the orientation device 1 in order to reflect the laser beam 71 in required directions as and with the required angular range, corresponding to the zone 80 to be treated.

In the ideal configuration a laser beam 71a will be conveyed by an optical fiber 72 from the outside as far as the distal end of the endoscope 70. For example, the optical fiber generates a laser beam 71a that is reflected by a prism 73 to return a laser beam 71b. In this case the mirror 31 is disposed so as to focus and then to reflect the laser beam 71b to return a laser beam 71c. The orientation of the plane mirror is guided by the microbot. Thus the microbot 60 directs the laser beam 71c onto the zones 80 to be treated, for example onto the vocal cords.

The spherical parallel kinematic microbot 60 with two degrees of freedom according to the invention makes it possible to address the constraints explained in the introduction to the present invention, namely, for a distance between the mirror 31 and the vocal cords of 20 mm:
- at least two degrees of freedom so as to be able to intervene over all of the zone 80 to be treated;
- an angular range of ±12.5° for each rotation axis of the mirror 31 so as to be able to intervene over all of the zone 80 to be treated;
- beam scanning resolution of 100 μm or better, which corresponds to a resolution of 0.15° for each rotation angle of the mirror 31 at the indicated distance of 20 mm, so as not to risk damaging healthy cells when treating malignant cells;
- beam movement bandwidth of at least 200 Hz;
- biocompatibility of all components of the microbot 60;
- volume occupied by the microbot 60 less than 10×10×10 $mm^3$.

In conclusion, the microbot according to the invention enables a response to the need for a device of small size (which is able to enter into the throat), able to sweep a laser beam over a defined angular range, and with two degrees of freedom, at high speed (so as not to remain for a long time in one position) and a relatively fine resolution (to distinguish healthy cells from malignant cells).

The microbot advantageously enables reception of at least one visualization system, for example a video camera, in order to verify the position of the laser beam, preferably the laser beam 71b, before it reaches the zone 80 to be treated.

The invention may find numerous applications, in particular for actuating a platform, said platform being able to receive a mirror for reflecting a laser beam. The laser beam may therefore be used for laser marking and/or etching, for 3D scanning, in the field of (micro)robotics (for example laser vision), in the field of telecommunications (for example for a variable optical attenuator or an optical switch), or for medical applications (relatively non-invasive endoscopic surgery, optical exploration with or without biopsy, etc.).

The microbot according to the invention may be used on drones, autonomous vehicles and more generally on mobile robots.

Figure 13:
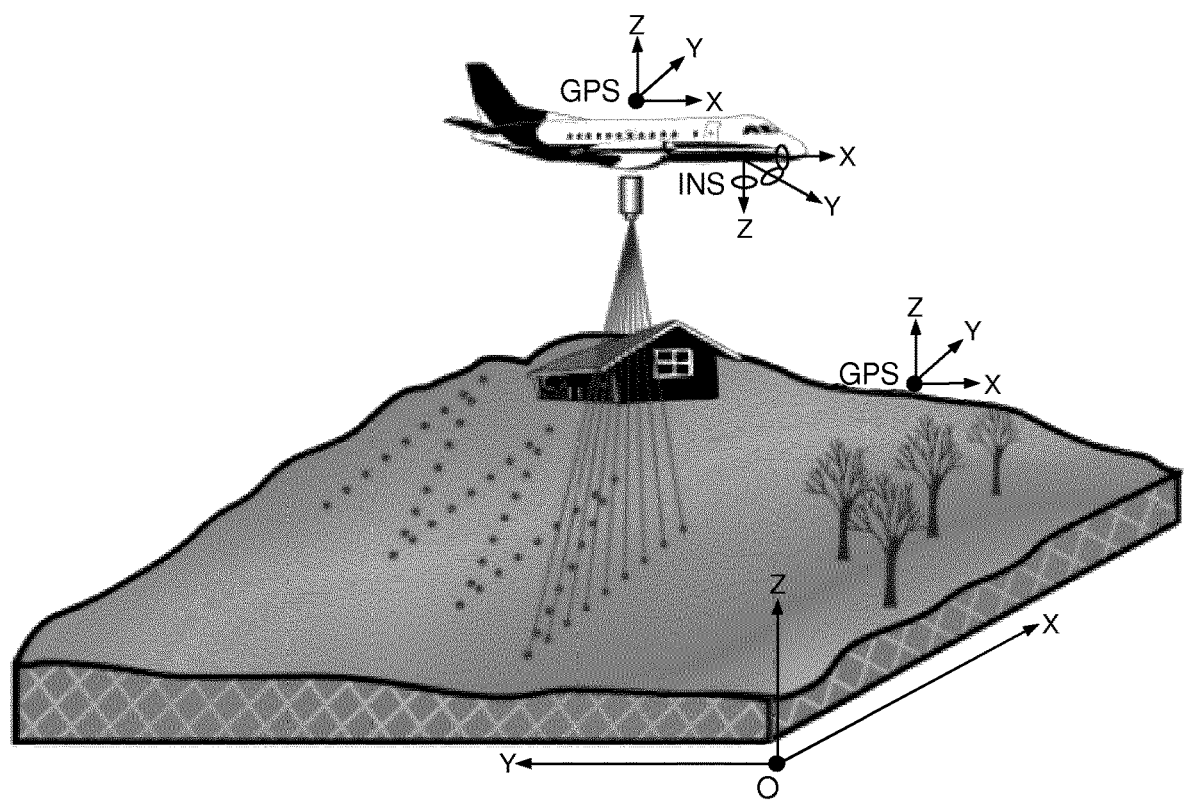
FIG. 13 shows a second example of application of the microbot according to the invention.

As shown in FIG. 13, one particular application of the microbot is to miniaturizing and making mobile LIDAR (Light Detection and Ranging) scanning devices. A LIDAR device scans a laser over the surface of a terrain to characterize its relief. The distance and the profile of the elements that appear on the surface of the terrain (houses, trees, cars, water, etc.) are calculated by interferometry. The microbot according to the invention is advantageously able to perform such scanning.

The invention claimed is:

1. A movement amplifying actuation device comprises:
   a first beam comprising a piezoelectric element, adapted to flex about a principal axis when a voltage is applied to it and adapted to be attached at a first end to a first fixed point;
   a second beam comprising a piezoelectric element, adapted to flex about said principal axis when a voltage is applied to it, and having a first end and a second end;
   a first articulation comprising:
      a first portion flexible about an axis perpendicular to the principal axis and connected to the first beam at the second end of said first beam,
      a second portion flexible about an axis perpendicular to the principal axis and connected to the second beam at the first end of said second beam,
      a first rigid portion connecting the first and second flexible portions,
      a second rigid portion adapted to be positioned against a second fixed point,
      a third portion flexible about an axis perpendicular to the principal axis connecting the second beam to the second rigid portion at a pivot point of said second beam so that the assembly formed by the second rigid portion and the second beam forms a lever about said pivot point,
      said flexible portions and rigid portions being parts of a one-piece component.

2. The movement amplifying actuation device as claimed in claim 1, further comprising:
   a third beam comprising a piezoelectric element, adapted to flex about the principal axis when a voltage is applied to it and having a first end and a second end;
   a second articulation comprising:
      a first portion flexible about an axis perpendicular to the principal axis and connected to the second beam at the second end of said second beam,
      a second portion flexible about an axis perpendicular to the principal axis and connected to the third beam at the first end of said third beam,
      a first rigid portion connecting the first and second flexible portions,
      a second rigid portion adapted to be positioned against a third fixed point,
      a third portion flexible about an axis perpendicular to the principal axis connecting the third beam to the second rigid portion at a pivot point of said third beam so that the assembly formed by the second rigid portion and the second beam forms a lever about said pivot point,
      said flexible portions and rigid portions being parts of a one-piece component.

3. The movement amplifying actuation device as claimed in claim 1, comprising:
   a first beam comprising a piezoelectric element, adapted to flex about a principal axis when a voltage is applied to it and adapted to be attached at a first end to a first fixed point;

N other beams, N being greater than or equal to 2 and M varying between 2 and N, each $M^{th}$ beam comprising a piezoelectric element and being adapted to flex about the principal axis when a voltage is applied to it, and having a first end and a second end; the $N^{th}$ beam having a free second end;

X articulations, X being equal to N-1 and Y being equal to M-1, each $Y^{th}$ articulation comprising:
- a first portion flexible about an axis perpendicular to the principal axis and connected to the $Y^{th}$ beam at the second end of said $Y^{th}$ beam,
- a second portion flexible about an axis perpendicular to the principal axis and connected to the $M^{th}$ at the first end of said $M^{th}$ beam,
- a first rigid portion connecting the first and second flexible portions,
- a second rigid portion adapted to be positioned against an $M^{th}$ fixed point,
- a third portion flexible about an axis perpendicular to the principal axis connecting the $M^{th}$ beam to the second rigid portion at a pivot point of said $M^{th}$ beam so that the assembly formed by the second rigid portion and the $M^{th}$ beam forms a lever about said pivot point;

said flexible portions and rigid portions being parts of a one-piece component.

4. The movement amplifying actuation device as claimed in claim 3, in which at least one $Y^{th}$ articulation further comprises a third rigid portion and a fourth rigid portion forming with the other parts of said articulation a one-piece component:
- the third rigid portion forming the connection between the first flexible portion of said $Y^{th}$ articulation and the $Y^{th}$ beam,
- the fourth rigid portion forming the connection between the second flexible portion of said $Y^{th}$ articulation and the $M^{th}$ beam.

5. The movement amplifying actuation device as claimed in claim 1, in which the flexible portions of at least one $Y^{th}$ articulation have parallel articulation axes perpendicular to the principal axis.

6. The movement amplifying actuation device as claimed in claim 1, in which the piezoelectric element comprises lead zirconate titanate.

7. The movement amplifying actuation device as claimed in claim 1, in which at least one beam has a bimorph structure.

8. A spherical parallel kinematic microbot with two degrees of freedom, comprising:
- an orientation device with two degrees of freedom comprising a platform to be oriented about a first rotation axis and a second rotation axis relative to a fixed base, a first actuation arm and a second actuation arm;
- first and second movement amplifying actuation devices as claimed in claim 1;
- the first actuation device being connected to the first actuation arm so as to transmit to it a first movement in translation relative to the fixed base so as to drive the platform in rotation about the first axis, and
- the second actuation device being connected to the second actuation arm so as to transmit to it a second movement in translation relative to the fixed base so as to drive the platform in rotation about the second axis.

9. The spherical parallel kinematic microbot as claimed in claim 8, in which the orientation device is a spherical orientation device with two degrees of freedom connecting the platform to two fixing points of a fixed base so as to be able to orient said platform in space by rotation about a first axis and a second axis, these two axes being substantially perpendicular and crossing at a center of spherical movement situated in said member to be oriented, comprising:
- a first actuation arm configured to effect a movement in translation relative to the fixed base and adapted to apply to a first transmission arm connected to a first fixing point of the fixed space by a flexible connection articulated about the first axis a movement in rotation relative to said fixed base so as to transmit to the platform a movement in rotation about said first axis;
- an intermediate arm connected to the first transmission arm by a flexible connection articulated about a third axis perpendicular to the first and second axes and connected to the platform by a flexible connection so as to transmit to the platform a movement in rotation about the first axis;
- a second actuation arm configured to effect a movement in translation relative to the fixed base and adapted to apply to a second transmission arm connected to a second fixing point of the fixed base by a flexible connection articulated about the second axis a movement in rotation relative to said fixed base so as to apply to the platform a movement in rotation about said second axis, said arm being connected to the platform by a flexible connection articulated about the first axis so as not to drive said second transmission arm in rotation about the first axis during actuation of the first actuation arm;
- the connection between the platform and intermediate arm being articulated about the axis so as not to drive said intermediate arm in rotation about the second axis during actuation of the second actuation arm;
- and the arms, the flexible connections and the platform forming the parts of a one-piece component forming the device, the arms and the platform being rigid portions of the device, and the flexible connections being flexible portions each forming a hinge about one only of the first, second and third axes, and connecting said rigid portions to one another, to the fixed base.

10. The spherical parallel kinematic microbot as claimed in claim 8, in which the rigid portions comprise a central layer of a flexible material, such as a polyimide, sandwiched between two layers of a rigid material, such as carbon fiber, the flexible connections being composed of the central layer.

11. The spherical parallel kinematic microbot as claimed in claim 8, in which one or more transmission arms and/or intermediate arms form a circular arc.

12. The spherical parallel kinematic microbot as claimed in claim 8, in which the spherical orientation device further comprises a flexible connection articulated about an axis parallel to the first axis and disposed between the first actuation arm and the first transmission arm and forming with the arms, the flexible connections and the platform a one-piece component.

13. The spherical parallel kinematic microbot as claimed in claim 8, the first actuation arm comprising a first portion adapted to be coupled to the actuation device and a second portion connected to the first transmission arm by a flexible connection articulated about an axis parallel to the first axis, said first and second portions and being connected by a flexible connection articulated about an axis parallel to the first axis and forming with the arms, the flexible connections and the platform a one-piece component.

14. The spherical parallel kinematic microbot as claimed in claim 8, the spherical orientation device further comprising a flexible connection connecting the second actuation arm and the second transmission arm articulated about an axis parallel to the second axis and forming with the arms, the flexible connections and the platform a one-piece component.

15. The spherical parallel kinematic microbot as claimed in claim 8, in which the spherical orientation device as claimed in claim 1 further comprises a universal joint type double flexible connection connecting the second actuation arm and the second transmission arm articulated about an axis parallel to the first axis and an axis parallel to the second axis and forming with the arms, the flexible connections and the platform a one-piece component.

16. The spherical parallel kinematic microbot as claimed in claim 8, in which the second actuation arm comprises a first portion adapted to be coupled to the actuation device and a second portion connected to the second transmission arm by a single flexible connection or a double flexible connection, the first and second portions and being connected to a universal joint type double flexible connection articulated about an axis parallel to the first axis and an axis parallel to the second axis, and forming with the arms, the flexible connections and the platform a one-piece component.

17. The spherical parallel kinematic microbot as claimed in claim 8, further comprising a support configured to create the fixed point of the actuation devices.

18. The spherical parallel kinematic microbot as claimed in claim 8, in which the platform supports a mirror.

19. The spherical parallel kinematic microbot as claimed in claim 18, in which the mirror is disposed so as to reflect a laser beam.

20. The spherical parallel kinematic microbot as claimed in claim 19, further comprising a device for viewing a spot of the laser beam positioned on a surface.

* * * * *